United States Patent
Dippl et al.

(10) Patent No.: US 7,452,129 B2
(45) Date of Patent: Nov. 18, 2008

(54) DRAWER FOR X-RAY DETECTORS

(75) Inventors: Thomas Dippl, Pressath (DE); Klaus Hruschka, Erbendorf (DE); Jochen Miguel Löseken, Bayreuth (DE); Peter Rauh, Schnabelwaid (DE); Josef Rupprecht, Erbendorf (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/996,861

(22) Filed: Nov. 24, 2004

(65) Prior Publication Data

US 2005/0148851 A1   Jul. 7, 2005

Related U.S. Application Data

(60) Provisional application No. 60/525,705, filed on Nov. 28, 2003.

(30) Foreign Application Priority Data

Nov. 28, 2003   (DE) ................................. 103 56 287

(51) Int. Cl.
G03B 42/02 (2006.01)
(52) U.S. Cl. ...................................... 378/177; 378/167
(58) Field of Classification Search ......... 378/172–174, 378/209, 37, 170, 181, 167, 169, 171, 182, 378/189, 177; 206/455
See application file for complete search history.

(56) References Cited

U.S. PATENT DOCUMENTS

| | | | | |
|---|---|---|---|---|
| 2,811,251 A | * | 10/1957 | Yerkovich | 378/205 |
| 3,826,922 A | * | 7/1974 | Ingles | 378/181 |
| 4,416,020 A | * | 11/1983 | Wagner et al. | 378/181 |
| 4,426,724 A | * | 1/1984 | Cutter | 378/181 |
| 4,894,854 A | * | 1/1990 | Guba et al. | 378/181 |
| 4,989,227 A | * | 1/1991 | Tirelli et al. | 378/177 |
| 5,148,466 A | * | 9/1992 | Fajac | 378/167 |

FOREIGN PATENT DOCUMENTS

| | | |
|---|---|---|
| DE | 29 11 911 A1 | 10/1979 |
| DE | 285 846 A5 | 1/1991 |
| WO | WO 01/33921 A1 | 10/2001 |

OTHER PUBLICATIONS

Translation of German Office Action, dated Jan. 26, 2006 on DE 103 56 287.7-54, Siemens.
German Office Action dated Jan. 27, 2006.

* cited by examiner

*Primary Examiner*—Hoon Song
(74) *Attorney, Agent, or Firm*—Brinks Hofer Gilson & Lione

(57) ABSTRACT

An X-ray detector drawer, into which an X-ray detector is insertable in two alternate orientations, has guide elements by which an inserted X-ray detector is fixedly positioned and oriented. The X-ray detector drawer has a securing device, by which an asymmetrical insertion of an X-ray detector with respect to either one of the two alternate orientations is hindered. The securing device includes a blocking element, whose position is altered as a function of the removal of the X-ray detector drawer. A receptacle for the X-ray detector drawer is configured to facilitate a removal the X-ray detector drawer from either of two opposite directions.

22 Claims, 2 Drawing Sheets

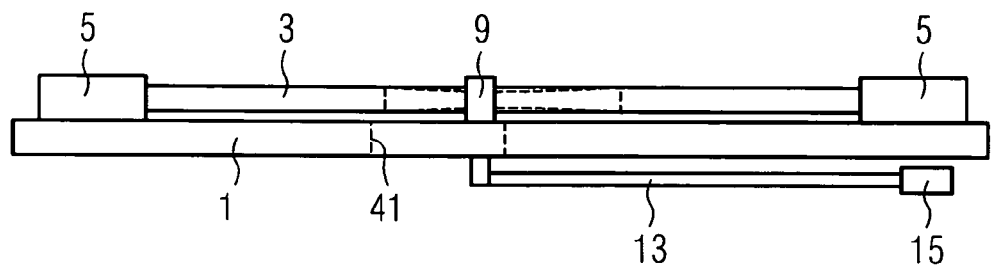
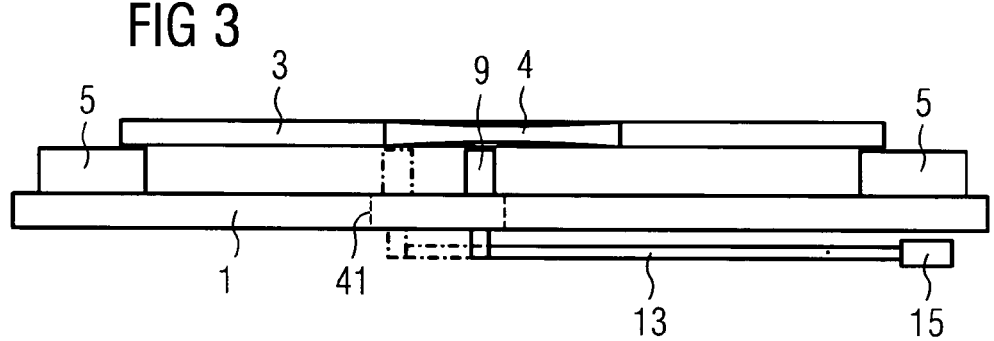
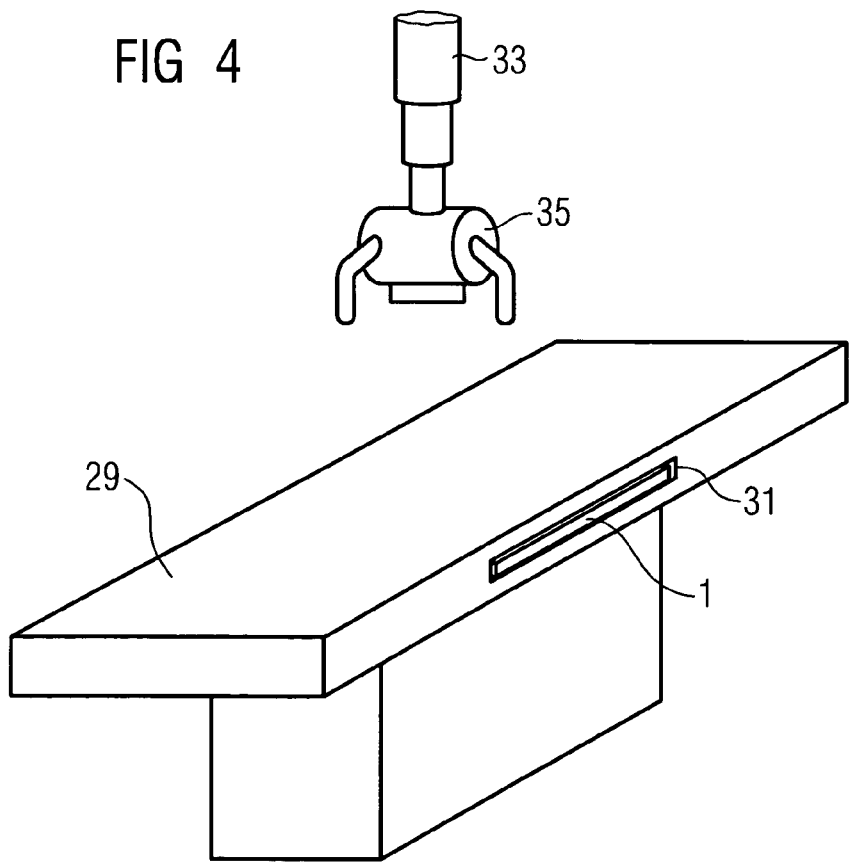

DRAWER FOR X-RAY DETECTORS

REFERENCE TO RELATED APPLICATIONS

The present patent document claims the benefit of the filing date under 35 U.S.C. §119(e) of provisional U.S. patent application Ser. No. 60/525,705, filed Nov. 28, 2003, which is hereby incorporated by reference.

BACKGROUND

The invention relates to, in general, to X-ray systems, and more particularly, to an X-ray detector drawer inside which an X-ray detector is insertable.

In X-ray systems, X-ray detector drawers are used so that X-ray detectors can be inserted interchangeably into patient examination tables, for example. The X-ray detectors may be digital flat panel detectors (FDs) or portable FDs. The detectors are available in various formats and sizes and are selected for the desired application and placed in the detector drawer in the orientation required for the applicable format (lengthwise, crosswise). Film sheet cassettes and memory sheet cassettes, after exposure to the X-radiation, are typically replaced with unexposed cassettes; flat detectors, at least for a change of format, are typically removed and rotated between lengthwise and crosswise orientations and inserted again. The removal and reinsertion are made substantially easier by detector drawers.

The advantage of digital X-ray detectors, such as the substantially rapid availability of image data, can be expanded by using portable detectors. These portable detectors enable, for instance, to take location-free X-ray images, in which the detector is not located in the detector drawer but instead is held by an equipment operator or user against the patient body part to be examined. In addition, switching between lengthwise and crosswise orientations is facilitated by the substantial ease of manipulation of portable detectors. There are a number of applications where a switch from one orientation to the other may be easily made by using portable detectors. The frequent changes of applications may mean that the detector has to be frequently inserted into and removed from the detector drawer.

A detector drawer for a flexible use and accommodation of a flat detector is disclosed, for instance, from WO 01/33921. In WO 01/33921, a mechanism is proposed for equipping an X-ray examination station or table with a digital detector and thus substantially simplifying switching of formats.

A substantial distinction between digital detectors and analog cassettes is that electrical cords are required for supplying power and transmitting information. When detector drawers are used, a potential risk may surface that these cords, which typically have mechanically vulnerable cord connections, may be sheared off or damaged upon insertion of the drawer, for example, because of careless or improper handling. This damaging problem arises typically in portable detectors, which are used in frequent changes among various applications and are correspondingly frequently inserted into the drawer.

The electrical connection of digital detectors represents an asymmetrical component of the detector construction in terms of the lengthwise and crosswise orientations. The same asymmetry is correspondingly true for a handle of the portable detector. Because of this asymmetry, the insertion of the detector may be one orientation in which the electrical connection is positioned advantageously with regard to potential damage due to over-use, and a converse orientation in which the electrical connection is disadvantageously positioned. In practical use, the equipment operator or user is advised therefore to take care to insert a digital detector in the appropriate orientation, which in everyday practical work may be a potential source of mistakes.

OBJECT AND SUMMARY

The present invention is defined by the appended claims. This description summarizes some aspects of the present embodiments and should not be used to limit the claims.

One object is to create an X-ray detector drawer in which a potential risk of inserting an X-ray detector in an unsuitable or unplanned orientation is substantially minimized or precluded.

An X-ray detector drawer is provided. An X-ray detector can be inserted in at least two contrary orientations; the X-ray detector drawer has guide elements by which an inserted X-ray detector may be fixed with regard to the assumed position and orientation. The X-ray detector drawer has a securing device with which an X-ray detector that is asymmetrical with regard to the two orientations can be substantially hindered from being inserted in one of those two orientations. As such, an advantage is that an asymmetrical X-ray detector may be inserted only in an orientation predetermined by the X-ray detector drawer, so there may not be need for an equipment operator to pay attention to the orientation upon insertion. This arrangement may enable the operator to work with the detector drawer and allows him to focus his concentration elsewhere, such as on a patient. The potential risk that a digital X-ray detector may be inserted in an orientation that may put the electrical connection at risk may be substantially reduced.

The securing device includes at least one blocking element, by which the insertion of a portion, which is asymmetrical with respect to at least two orientations, of the contour of an X-ray detector can be substantially blocked. As such, the fact that the X-ray detector itself has an asymmetrical outline is exploited in a substantially simple way or fashion. Positioning the blocking element in a way that takes this asymmetrical outline into account is a desirably easy way to reduce potential inappropriate insertions, because the blocking element may get in the way of the asymmetrical part of the detector outline upon insertion.

The position of the blocking element may be variable automatically as a function of the removal, i.e., pulling out, of the X-ray detector drawer from a receptacle. As such, a mechanism may be created which positions the blocking element as a function of the direction in which the drawer is pulled out of the receptacle, so that the blocking element may be automatically adjusted to a plurality of alternate requirements. For example, the X-ray detector may need to be inserted in alternate orientations, depending on the side from which the drawer was pulled out. However, in a further feature, positioning of the blocking element may also be done as a function of how far the drawer has been pulled out from the receptacle, so that for instance automatically, an alternate position may result when the drawer has been pulled further out, for example, for inserting a detector of lengthwise format, as opposed to a drawer not pulled as far out, for inserting in crosswise format, for example.

The X-ray detector drawer may be pulled out in two opposed directions. As such, the detector may be used, for example, in patient examination tables in which the actuating device of the drawer and, hence, the side of the table from which the detector is to be inserted, are adapted flexibly to the given application. Patient examination tables that have a drawer that can be pulled out from either side are used in radiology and urology, among other fields, or in the surgical environment in general.

The securing device may include two blocking elements. Via these two alternately positioned blocking elements, a drawer may be provided such that one of two predetermined orientations of the detector may be blocked in two opposed directions of removal blocks.

Illustrative and exemplary embodiments of the invention are described in further detail below with reference to and in conjunction with the figures.

BRIEF DESCRIPTION OF THE DRAWINGS

FIG. 2 is a schematic side view of the drawer with a detector of FIG. 1 and a blocking element;

FIG. 3 is a schematic side view of the detector drawer of FIG. 1 with a blocking element and with a detector blocked by the blocking element; and FIG. 4 illustrates an embodiment of an X-ray system with an X-ray detector drawer.

DETAILED DESCRIPTION OF THE DRAWINGS

Figure 1:
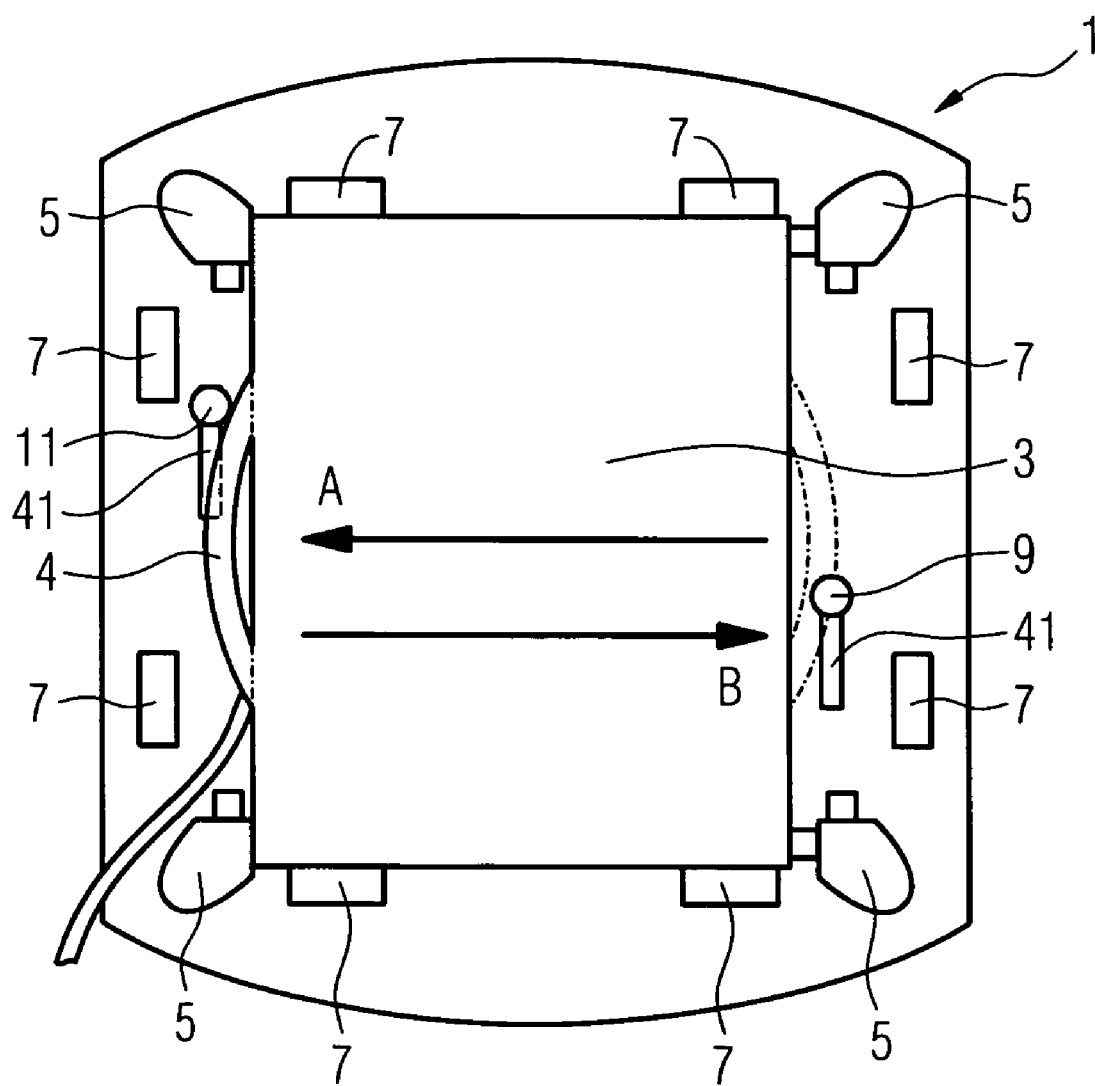
FIG. 1 is a schematic plan view on an X-ray detector drawer with a detector in one embodiment.

In FIG. 1, an X-ray detector drawer 1 is shown schematically in a plan view. An X-ray detector 3 has been inserted into or placed inside, the detector drawer 1. The X-ray detector 3 is a digital portable flat detector, which has a handle 4. The X-ray detector 3 is supplied with electrical power via an electrical cable, which is connected in the region of the handle 4, and transmits image information via this cable.

The handle 4 and the electrical cable may represent asymmetrical parts of the outline of the detector 3, with respect to the contrary orientations A and B indicated by arrows. By a rotation of 180°, the handle 4 and cable may come to rest on the other side relative to the indicated orientations A, B, which is shown in the drawing by dashed lines.

The detector 3 may be fixed in its position in the detector drawer 1 by guide elements 5, 7; and moreover simultaneously may be fixed with respect to the alternate orientations A, B. Once inserted or placed in the detector drawer 1, the detector 3 may be accordingly firmly held in the inserted position by the guide elements 5, 7.

The detector drawer 1 has a securing device, which includes two blocking elements 9, 11. One can see that, on the left in the FIG. 1 drawing, the blocking element 11 may be disposed next to the handle 4 of the inserted detector 3. Thus, the blocking element 11 may not block the insertion of the handle 4, and so the detector 3 may be placed unhindered in the orientation shown in the drawing. In the orientation shown, the electrical cable may come to rest in the position shown, at the bottom left in the drawing. With regard to an insertion direction of the detector drawer 1, for instance into a receptacle, in the direction away from the cable or in other words upward in the drawing, this arrangement may minimize the potential risk that the cable will be sheared off.

Inserting the detector 3 in the unsuitable, or contrary orientation, with the handle 4 to the right in the drawing, may be hindered by the blocking element 9 located on the right. As one can see from the contour shown in dashed lines of the detector 1 oriented the unsuitable way, in this orientation the blocking element 9 and the handle 4 may come to rest substantially one above the other, and so the detector 3 may rest on the blocking element 9, instead of being inserted. This arrangement may hinder insertion with the unsuitable orientation, and the electrical cable may desirably not come to rest at an unfavorable location, namely at the top right in the drawing. Otherwise, if the drawer 1 were to move in the direction described above, the cable may substantially easily become sheared off.

In FIG. 1, the blocking element 9 may be supported in a guide 41. The same arrangement may be true for the blocking element 11, but whose guide 41 may be thereby partly concealed by the handle 4. The position of both blocking elements 9, 11 may be varied as a function of the pulling out of the drawer 1. In the state shown in the drawing, an assumption is that the drawer 1 is pulled in the direction downward toward the cable. When the drawer 1 is pulled in the other, opposite direction, the blocking element 9 may be moved substantially automatically to the other end of the guide 41 shown, via a mechanism not further shown in the FIG. 1 drawing. A similar mechanism is correspondingly configured for the other blocking element 11. As such, when the drawer 1 is pulled in the other direction, the two blocking elements 9, 11 may adopt correspondingly predetermined alternate positions, in such a way that the detector 3 can be inserted only with the opposite orientation. As such, depending on the direction in which the drawer 1 is pulled out, an alternate position results for the electrical cable, so that independently of the direction in which the drawer 1 is pulled out, the electrical cable may not come to rest in a position which may include a potential risk of being sheared off.

In FIG. 2, the detector drawer 1 is shown schematically with the detector 3 inserted, in a side view, from the handle-free side of the detector 3. The detector 3 is fixed in one of only a single or multiple predetermined positions and orientations by the guide elements 5. The detector 3 is inserted with the suitably appropriate orientation, so as to come to rest next to the blocking element 9 that is not visible in the drawing and is not blocked by that blocking element.

From FIG. 1, the blocking element 9 is supported longitudinally displaceably in a guide 41, and the guide 41 may extend from right to left in the plane of the drawing and is represented by dashed lines. Underneath the drawer 1, the blocking element 9 is connected to a slide 13 which may slide the blocking element back and forth in the guide 14. The slide 13 has a driver 15, which upon displacement of the drawer 1, for instance into a receptacle, may engage a corresponding slaving mechanism in the receptacle for the drawer 1. The slaving mechanism, not shown in detail, may be designed or configured such that the blocking element 9 may be displaced into one or another terminal position of the guide 41, depending on the direction in which the drawer 1 is pulled out.

In FIG. 3, the detector drawer 1 is shown with the detector 3 oriented conversely and therefore not appropriately placed. In the inappropriate and unsuitable orientation, the handle 4 may rest on the blocking element 9, so that the detector 3 may not be appropriately inserted into the drawer 1.

The position of the blocking element 9 on the other end of the guide 41 shown in dashed lines is also shown in dashed lines in the drawing. On the assumption that in the state shown in the drawing, the drawer 1 was pulled out of the receptacle toward the left, the position shown in dashed lines may be established by pulling the drawing out of the receptacle in the opposite direction, to the right. In the position shown in dashed lines, the blocking element 9 may no longer hinder the handle 4. Thus, into the drawer 1 which has been pulled out in the opposite direction, the detector 3 may be inserted only in what is in turn an opposite orientation to that, without being blocked. As such, the cable of the detector 3, even with the drawer pulled out in that direction, may come to rest away from the receptacle of the drawer 1 and therefore may not be undesirably sheared off or pulled on when the drawer 1 is inserted again.

In FIG. 4, an X-ray system with a detector drawer 1 is shown. The detector drawer 1 is located in a receptacle 31 of a patient examination table 29. From the patient examination table 29, the detector drawer 1 can be pulled out of the receptacle 31 in both opposite directions, to the right and to the left in the drawing, for removal or insertion of the detector 3; in the drawing, only the right-hand side is visible.

An X-ray emitter or source 35 secured to a ceiling mount 33 is located above the patient examination table 29. Via the X-ray emitter 35, a patient lying on the patient examination table 29 may be X-rayed, so that the X-ray detector 3 placed underneath the table 29 in the detector drawer 1 may be exposed.

Pulling the detector drawer 1 out of the receptacle 31 in one direction or another may cause the slaving mechanism, referred to in the description of the preceding drawings, to move the blocking elements 9, 11, also described above, into the respective terminal positions of their guides 41. Thus, such detector 3 described above may be inserted substantially automatically in only one of the two orientations, depending on the side of the patient examination table 29 on which the drawer 1 is located at that time. The desirably suitable orientation may be selected such that shearing off of the electrical cable of the X-ray detector 3 as the drawer 1 is pushed into the receptacle 31 is substantially minimized.

The invention claimed is:

1. An X-ray detector drawer, comprising:
 a guide elements disposed to fixedly hold an X-ray detector inserted in a plurality of predetermined orientations; and
 a blocking element positionable to prevent insertion of the X-ray detector in all but one of the plurality of predetermined orientations.

2. The X-ray detector drawer of claim 1, wherein the insertion of a portion of a contour of an X-ray detector is hindered, the portion of the contour of the X-ray detector being asymmetrical with respect to the at least one of two predetermined orientations of the plurality of predetermined orientations.

3. The X-ray detector drawer of claim 1, wherein a position of the blocking element is altered as a function of a removal of the X-ray detector drawer from a receptacle.

4. The X-ray detector drawer of claim 2, wherein a position of the at least one blocking element is altered as a function of a removal of the X-ray detector drawer from a receptacle.

5. The X-ray detector drawer of claim 4, wherein the receptacle is configured to facilitate a removal the X-ray detector drawer from either of two opposite directions.

6. The X-ray detector drawer of claim 1, comprising two blocking elements.

7. The X-ray detector drawer of claim 2, wherein the at least one of the blocking elements is displaceable into one of two predetermined positions as a function of the direction in which the X-ray detector drawer is pulled out of a receptacle.

8. The X-ray detector drawer of claim 6, wherein the two blocking elements are each displaceable into one of two predetermined positions as a function of the direction in which the X-ray detector drawer is pulled out of a receptacle.

9. A patient examination table having a receptacle into which an X-ray detector drawer is insertable, the patient examination table comprising:
 the X-ray detector drawer into which an X-ray detector is insertable in one of two alternate predetermined orientations;
 a plurality of guide elements by which an inserted X-ray detector is fixedly positioned and oriented; and
 a blocking element disposable to prevent an unsuitable insertion of the X-ray detector with respect to either one of the two alternate predetermined orientations.

10. The patient examination table of claim 9, wherein the insertion of a portion of a contour of the X-ray detector is prevented, the portion of the contour of the X-ray detector being asymmetrical with respect to the two alternate predetermined orientations.

11. The patient examination table of claim 10, wherein a position of the at least one blocking element is automatically altered as a function of a removal of the X-ray detector drawer from a receptacle.

12. The patient examination table of claim 11, wherein the receptacle is configured to facilitate a removal the X-ray detector drawer from either of two opposite directions.

13. The patient examination table of claim 9, comprising two blocking elements.

14. The X-ray detector drawer of claim 10, wherein the at least one blocking elements is displaceable into one of two positions as a function of the direction in which the X-ray detector drawer is pulled out of a receptacle.

15. The X-ray detector drawer of claim 12, wherein two blocking elements are each displaceable into one of two positions as a function of the direction in which the X-ray detector drawer is pulled out of a receptacle.

16. An X-ray system comprising:
 a patient examination table having a receptacle into which an X-ray detector drawer is insertable in one of two alternate predetermined orientations;
 a plurality of guide elements by which an inserted X-ray detector is fixedly positioned and oriented; and
 a blocking element positionable to automatically prevent insertion of the X-ray detector with respect to one of the two alternate predetermined orientations.

17. The X-ray system of claim 16, wherein the insertion of a portion of a contour of the X-ray detector is prevented, the portion of the contour of the X-ray detector being asymmetrical with respect to the two alternate predetermined orientations.

18. The X-ray system of claim 17, wherein a position of the blocking element is automatically altered as a function of a removal of the X-ray detector drawer from the receptacle.

19. The X-ray system of claim 18, wherein the receptacle is configured to facilitate the removal the X-ray detector drawer from either of two opposite directions.

20. The X-ray detector drawer of claim 16, wherein the blocking element is displaceable into one of two predetermined positions as a function of the direction in which the X-ray detector drawer is pulled out of the receptacle.

21. An X-ray detector drawer into which an X-ray detector having an asymmetrical shape can be inserted in at least a first and a second predetermined orientation, comprising;
 guide elements fixing the inserted X-ray detector in position; and
 a blocking element having a first state to prevent insertion of the X-ray detector in the first predetermined orientation while permitting the insertion of the X-ray detector in the second predetermined orientation, and a second state of all the blocking element to prevent insertion the X-ray detector in the second predetermined orientation while permitting the insertion of the X-ray detector in the first predetermined orientation.

22. The X-ray detector drawer of claim 21, wherein the first state and the second state configuration are determined based on a direction in which the X-ray detector drawer is pulled out of a receptacle.

* * * * *

UNITED STATES PATENT AND TRADEMARK OFFICE
CERTIFICATE OF CORRECTION

PATENT NO. : 7,452,129 B2
APPLICATION NO. : 10/996861
DATED : November 18, 2008
INVENTOR(S) : Thomas Dippl et al.

It is certified that error appears in the above-identified patent and that said Letters Patent is hereby corrected as shown below:

In the Claims

In column 5, claim 1, line 31, after "a guide" delete "elements" and substitute --element-- in its place.

In column 6, claim 21, line 59, before "the blocking element" delete "all".

Signed and Sealed this

Sixteenth Day of June, 2009

JOHN DOLL
*Acting Director of the United States Patent and Trademark Office*